(12) United States Patent
Harada

(10) Patent No.: US 9,395,307 B2
(45) Date of Patent: Jul. 19, 2016

(54) DEVICE AND METHOD FOR MEASURING INFILTRATION

(71) Applicant: Yoshihiro Harada, Kanagawa (JP)

(72) Inventor: Yoshihiro Harada, Kanagawa (JP)

(73) Assignee: RICOH COMPANY, LTD., Tokyo (JP)

( * ) Notice: Subject to any disclaimer, the term of this patent is extended or adjusted under 35 U.S.C. 154(b) by 33 days.

(21) Appl. No.: 14/299,289

(22) Filed: Jun. 9, 2014

(65) Prior Publication Data

US 2014/0374604 A1    Dec. 25, 2014

(30) Foreign Application Priority Data

Jun. 24, 2013    (JP) .................. 2013-131282

(51) Int. Cl.
| | |
|---|---|
| *G01J 5/02* | (2006.01) |
| *G01N 21/85* | (2006.01) |
| *G01N 15/08* | (2006.01) |
| *G01N 21/86* | (2006.01) |

(52) U.S. Cl.
CPC ............ *G01N 21/85* (2013.01); *G01N 15/0826* (2013.01); *G01N 21/86* (2013.01)

(58) Field of Classification Search
CPC ......... G01N 21/85; G01N 21/255; G01B 9/02
USPC ....................................................... 250/353
See application file for complete search history.

(56) References Cited

U.S. PATENT DOCUMENTS

| | | | | |
|---|---|---|---|---|
| 6,449,039 B1 * | 9/2002 | Bouzid | ................ | G02B 21/002 250/458.1 |
| 2006/0183992 A1 * | 8/2006 | Kawashima | ............. | A61B 5/06 600/407 |
| 2007/0268427 A1 * | 11/2007 | Uehara | ................ | G02B 6/0016 349/62 |
| 2008/0140325 A1 * | 6/2008 | Teramura | ........... | G01N 21/4795 702/57 |
| 2011/0064271 A1 * | 3/2011 | Wang | .................... | G06T 7/0024 382/103 |

FOREIGN PATENT DOCUMENTS

| | | |
|---|---|---|
| JP | 2004-333228 | 11/2004 |
| JP | 2005-127938 | 5/2005 |
| JP | 2009-126941 | 6/2009 |
| JP | 2010-229566 | 10/2010 |
| JP | 2010-229566 A | * 10/2010 |

OTHER PUBLICATIONS

English Machine Translation of JP 2010-229566 A, Mikiko et al. (Oct. 2010).*

* cited by examiner

*Primary Examiner* — David Porta
*Assistant Examiner* — Abra Fein
(74) *Attorney, Agent, or Firm* — Harness, Dickey & Pierce, PLC

(57) ABSTRACT

An infiltration measuring device includes a light source, an optical splitter to split a light beam from the light source into a reference light beam and a measuring light beam, a reference optical system provided in an optical path of the reference light beam, a measuring optical system provided in an optical path of the measuring light beam to measure a target object, an optical combiner to combine an optical feedback from the target object with a light beam from the reference optical system, a detector to detect the light beam combined by the optical combiner and convert the combined light beam into a photoelectric conversion signal, an imager to image a cross section of the target object on the basis of the photoelectric conversion signal, a display to display a cross-sectional image formed by the imager, and an applicator to apply an infiltrative material onto the target object.

9 Claims, 4 Drawing Sheets

DEVICE AND METHOD FOR MEASURING INFILTRATION

CROSS REFERENCE TO RELATED APPLICATION

The present application is based on and claims priority from Japanese Patent Application No. 2013-131282, filed on Jun. 24, 2013, the disclosure of which is hereby incorporated by reference in its entirety.

BACKGROUND OF THE INVENTION

1. Field of the Invention

The present invention relates to infiltration measuring device and method for observing, with time, an infiltration of an infiltrative material as fluid into the surface of a target object such as a sheet-like medium including film or coated paper without damaging the target object.

2. Description of the Related Art

There is a printer which generates a functional component as document, image, or electric circuit by attaching a fluid as ink onto a printed material as sheet-like medium. Such a printer evaluates a fluid infiltration into the sheet-like medium along thickness.

The evaluation of the fluid infiltration can be used, for example, for improving image quality, optimizing an amount of applied fluid, and enhancing reliability of a functional component. Japanese Patent Application Publication No. 2005-127938 (Reference 1) discloses cutting a fluid permeated object such as a printed material and observing a cross section of the object with a mass spectrometer or a scanning electron microscope for evaluation, for example.

In Reference 1 the surface of the target object is cut at a certain angle to capture an image of the cut surface and evaluate an infiltrated state of fluid in the target object.

However, there may be a possibility that the target object is damaged or destroyed by cutting. In view of this, the target object is embedded into a resin and frozen before cutting.

Further, Japanese Patent Application Publication No. 2004-333228 (Reference 2), for instance, discloses making a fluid infiltrated in the target object fluorescent with a laser beam, detecting a fluorescence with a co-focal optical system and converting it to a photoelectric detection signal to form an image of the infiltrated fluid along the thickness of the target object. By this technique the infiltrated state of fluid can be measured without cutting the target object.

The technique in Reference 1 is a destructive testing so that it cannot continuously observe a temporal change in the fluid infiltration with time.

Meanwhile, the technique in Reference 2 is a non-destructive testing and able to continuously observe a temporal change in the fluid infiltration with time.

However, this technique needs to detect a feeble fluorescence. If the target object is a paper and an infiltrated fluid is ink, for example, it is not possible to detect a fluorescence from a deep portion of the paper due to a large scattering effect by a paper surface. Thus, only the infiltration near the paper surface is observable.

SUMMARY OF THE INVENTION

The present invention aims to provide an infiltration measuring device and method for continuously observing an infiltration of an infiltrative material into a deep portion of a target object without damaging or destroying the target object.

According to one embodiment, an infiltration measuring device which measures an infiltration of an infiltrative material into a target object, comprises a light source, an optical splitter to split a light beam from the light source into a reference light beam and a measuring light beam, a reference optical system provided in an optical path of the reference light beam, a measuring optical system provided in an optical path of the measuring light beam to measure the target object, an optical combiner to combine an optical feedback from the target object with a light beam from the reference optical system, a detector to detect the light beam combined by the optical combiner and convert the combined light beam into a photoelectric conversion signal, an imager to image a cross section of the target object on the basis of the photoelectric conversion signal, a display to display a cross-sectional image formed by the imager, and an applicator to apply the infiltrative material onto the target object.

BRIEF DESCRIPTION OF THE DRAWINGS

Features, embodiments, and advantages of the present invention will become apparent from the following detailed description with reference to the accompanying drawings.

DETAILED DESCRIPTION OF THE PREFERRED EMBODIMENTS

Hereinafter, an embodiment of infiltration measuring device and method will be described in detail with reference to the accompanying drawings. Wherever possible, the same reference numbers will be used throughout the drawings to refer to the same or like parts.

Figure 1:
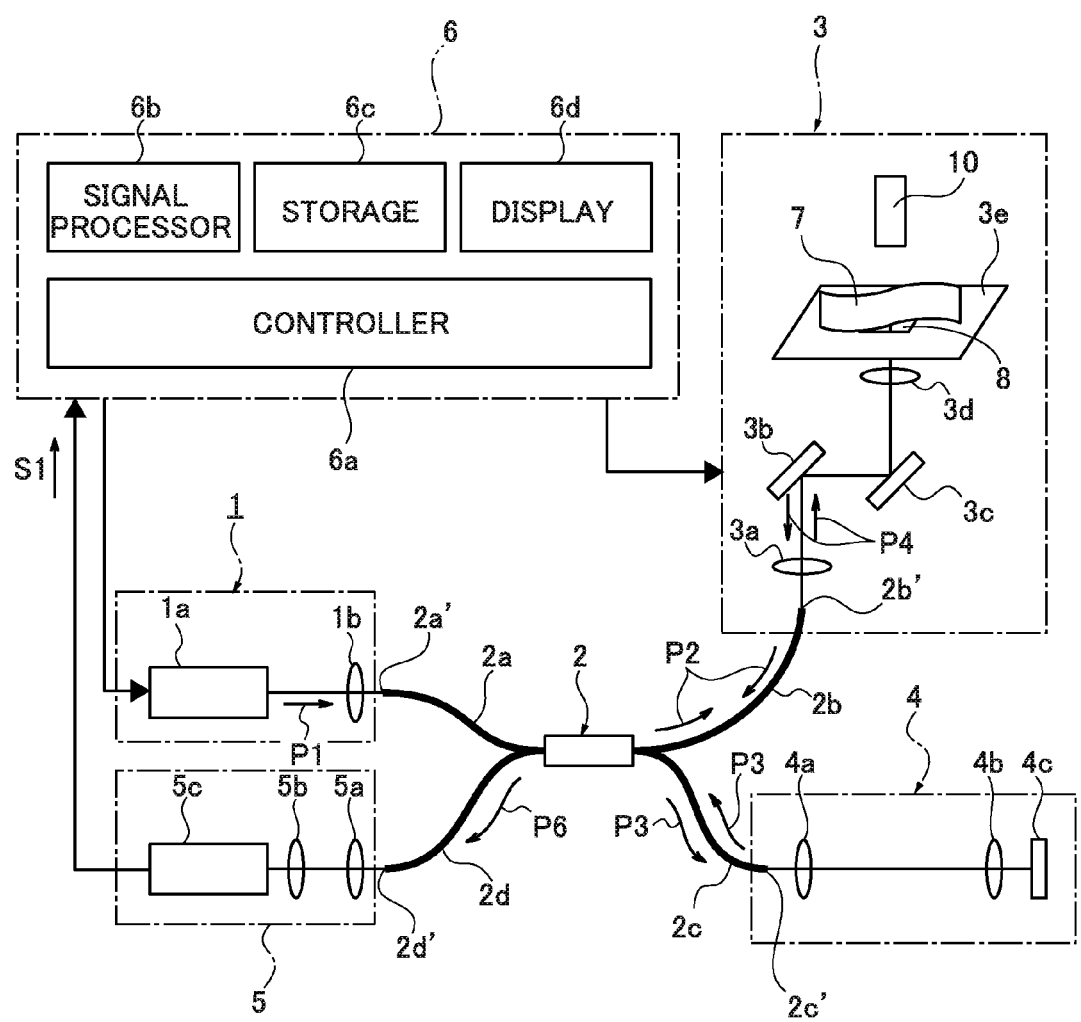
FIG. 1 is a block diagram of the structure of the essential part of an infiltration measuring device according to one embodiment of the present invention.

FIG. 1 is a block diagram of the structure of the essential part of an infiltration measuring device. The infiltration measuring device in FIG. 1 comprises a light source unit 1, an optical combiner/splitter 2, a measuring optical system 3, a reference optical system 4, a detector 5, and a signal processing controller 6.

The light source unit 1 comprises a light source 1a and a condenser lens 1b. The light source 1a emits a wide-band light beam P1 having a center wavelength in a near-infrared wavelength band from 0.7 to 2.0 micrometers and a coherent length of 20 micrometers or less. The wide-band light beam P1 has partial coherence, and it is gathered by the condenser lens 1b, converged at an incidence end 2a' of an optical guide fiber 2a and guided to the optical combiner/splitter 2 via the optical guide fiber 2a.

The optical combiner/splitter 2 comprises a fiber coupler, for example. The wide-band light beam P1 is split into a measuring light beam P2 and a reference light beam P3 by the optical combiner/splitter 2. For instance, the light amount of the wide-band light beam P1 incident on the fiber coupler is split at the ratio of 1 to 1. The measuring light beam P2 is guided to an optical guide fiber 2b as a measuring optical path while the reference light beam P3 is guided to an optical guide fiber 2c as a reference optical path. The optical combiner/splitter 2 functions as an optical splitter to split the light from the light source unit 1 into the measuring light beam P2 and reference light beam P3 and as an optical combiner to combine reflected and scattered light of the measuring light beam P2 by a target object 7 and the reference light beam P3, as later described.

The measuring optical system 3 comprises a collimate lens 3a, a galvanometer mirrors (galvanometer scanner) 3b, 3c, a collimate lens 3d, and a specimen mount 3e. The target object 7 is placed on the specimen mount 3e having a window 8. The target object 7 is for example a printed material as a sheet-like medium including film and paper.

The collimate lens 3a faces an incidence/exit end 2b' of the optical guide fiber 2b to gather the measuring light beam P2 from the optical guide fiber 2b and convert it to a parallel light beam P4. The parallel light beam P4 is guided to the galvanometer mirrors 3b, 3c.

Figure 2:
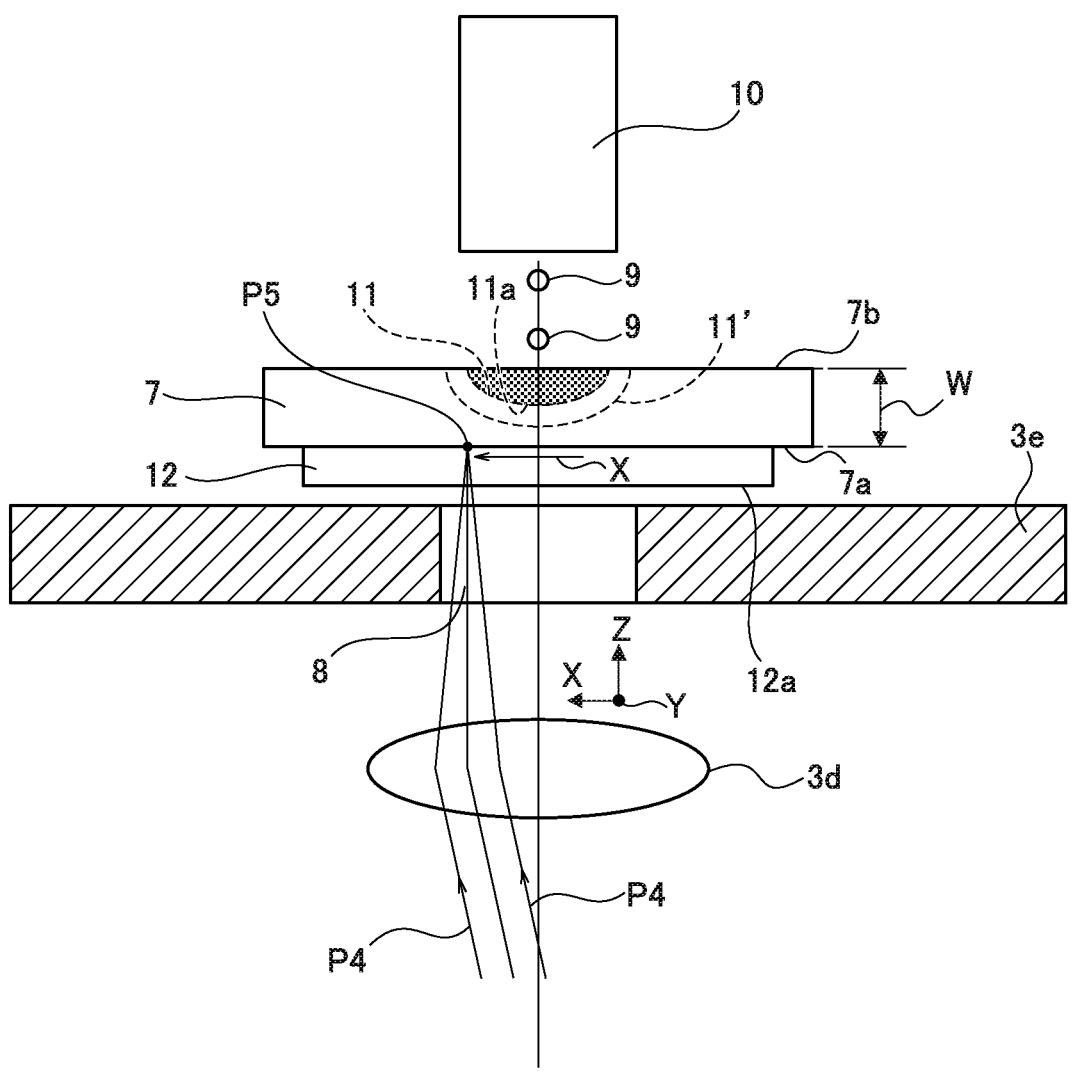
FIG. 2 is a partial enlarged view of a measuring optical system in FIG. 1.

Both of the galvanometer mirrors 3b, 3c are reciprocatively oscillated. Three-dimensional cross-sectional image data can be obtained by driving the galvanometer mirrors 3b, 3c together, as later described. One-dimensional cross-sectional image data can be obtained by driving either of the galvanometer mirrors 3b, 3c. The parallel light beam P4 is guided to the collimate lens 3d as scanning light. The collimate lens 3d functions to convert the scanning light to a spot light beam P5 and it forms the spot light beam P5 by adjusting the parallel light beam P4 to be constantly incident on the target object vertically, as shown in FIG. 2. Thus, it is able to obtain an accurate cross-sectional image of the target object by making the parallel light beam P4 be incident on the target object 7 vertically.

The front surface 7a of the target object is two-dimensionally scanned with the spot light beam P5 through the window 8 in FIG. 2. In FIG. 2 the arrow Z indicates the optical axis of the collimate lens 3d and the arrow X indicates a scan direction orthogonal to the optical axis Z. The measuring optical system 3 comprises an applicator 10 to apply an infiltrative material 9 onto the target object 7. Herein, the applicator 10 is a fluid discharger to quantitatively discharge a fluid to the target object 7. The infiltrative material 9 is ink, for example.

The infiltrative material 9 is infiltrated into the target object 7 over time. An area 11 of the target object 7 in FIG. 2 is an infiltrated area of the infiltrative material 9 at time $t_2$ when time $\Delta t$ has elapsed from time $t_1$ at which the infiltrative material 9 is attached to the back surface 7b of the target object 7.

An area 11' is an infiltrated area of the infiltrative material 9 at time $t_3$ when time $\Delta t'$ ($\Delta t' > \Delta t$) has elapsed since the infiltrative material 9 is attached to the back surface 7b of the target object 7. The infiltrated area of the infiltrative material 9 deepens or is infiltrated along the thickness of the target object 7 with time. The measurement of the infiltration of the infiltrative material 9 is described later.

The scan spot light beam P5 is partially scattered and reflected by the front surface 7a of the target object and the rest thereof reaches inside the target object 7 or is absorbed into the target object 7.

A part of the scan spot light P5 having reached inside the target object 7 is reflected by the interface 11a of the infiltrated area 11 and the rest thereof is refracted by the interface 11a to the inside of the infiltrated area 11. Herein, the infiltrated area 11 is defined to be an area inside the target object 7 with voids filled with the infiltrative material 9. The interface 11a is an interface between an area with voids not filled with the infiltrative material 9 and the infiltrated area 11.

The light reflected by the interface 11a and the light reflected and scattered by the front surface 7a are collected by the collimate lens 3d to be the parallel light beam P4 (optical feedback) or the measuring light beam P2 and guided to the galvanometer mirrors 3b, 3c.

Then, the measuring light beam P2 is converged by the collimate lens 3a and guided to the incidence/exit end 2b' of the optical guide fiber 2b to reach the optical combiner/splitter 2 through the optical guide fiber 2b.

The reference optical system 4 comprises collimate lenses 4a, 4b, and a reference mirror 4c. The collimate lens 4a faces an incidence/exit end 2c' of an optical guide fiber 2c and functions to convert the reference light beam P3 from the incidence/exit end 2c' into a parallel light beam. The reference light beam P3 is collected and guided by the collimate lens 4 to the reference mirror 4c and totally reflected thereby.

The reference light beam P3 reflected by the reference mirror 4c is guided to the optical combiner/splitter 2 via the optical guide fiber 2c. Then, the measuring light beam P2 and reference light beam P3 from the optical guide fibers 2b, 2c are combined by the optical combiner/splitter 2 to become an interfering light beam P6 and be guided to the detector 5 via the optical guide fiber 2d. Note that the optical path length from the optical combiner/splitter 2 to the target object 7 is equal to that from the reference mirror 4c to the optical combiner/splitter 2. However, they can be different as long as a cross-sectional image of the target object 7 can be obtained.

The detector 5 comprises condenser lenses 5a, 5b and a photoelectric conversion element 5c. The interfering light beam P6 is output from the exit end 2d' of the optical guide fiber 2d, collected by the condenser lens 5a to be a parallel light beam and guided to the condenser lens 5b, and converged on the photoelectric conversion element 5c.

The photoelectric conversion element 5c photoelectrically converts the interfering light beam P6 into a photoelectric conversion signal S1 and outputs it to the signal processing controller 6. The signal processing controller 6 comprises a controller 6a, a signal processor 6b, a storage 6c, and a display 6d. The controller 6a properly controls the light emission of the light source 1a, the oscillation of the galvanometer mirrors 3b, 3c, the discharge of the fluid discharger, and timing at which the photoelectric conversion signal S1 is acquired. It also controls the signal processor 6b, storage 6c, and display 6d properly.

The controller 6a comprises hardware such as CPU, ROM, RAM and a certain control program. The signal processor 6b as imager processes the photoelectric conversion signal S1 by a software program in compliance with optical coherence tomography, to generate a cross-sectional image of the target object according to image intensity data or brightness data based on the photoelectric conversion signal S1.

In the following the generation of a cross-sectional image by optical coherence tomography is described. Optical coherence tomography uses, for example, an optical sensor comprising a spectroscopic element (not shown) as the photoelectric conversion element 5c and a line sensor (not shown). The optical sensor can detect spectrum in the entire wavelength band of the light from the light source 1. The interfering light beam P6 includes the measuring light beam P2 as optical feedback from the surface or inside of the target object 7 and the reference light beam P3. The optical sensor can detect spectrum interference if optical feedback occurs only from a position in optical path length equal to that from the optical combiner/splitter 2 to the reference mirror 4c in the measuring optical system 3. Further, when the position where optical feedback occurs is moved in one direction in the measuring optical system 3 with the optical path length from the optical combiner/splitter 2 to the reference mirror 4c fixed, the interval of interference patterns of the interference spectrum is narrowed as a difference in the optical path lengths is increased. That is, the interval of interference patterns is determined by the position at which optical feedback occurs.

The interfering light beam P6 includes optical feedbacks from all the positions on the surface and inside of the target object 7 so that the interference patterns with all different intervals appear in the spectrum interference detected. The signal processor 6b performs Fourier transform on the photoelectric conversion signal S1 having this spectrum interference. Thereby, the interference patterns with all different intervals in the spectrum interference are resolved to be able to specify the position in which the optical feedback occurs. The amplitude of the spectrum interference is determined by the intensity of the optical feedback. If the intensity of a Fourier transformed signal corresponding to some position of the occurrence of the optical feedback is relatively large, the intensity of reflected or scattered light at this position is relatively large. Thus, a distribution of the target object 7 along the thickness can be acquired as a one-dimensional cross-sectional image by determining a brightness distribution in accordance with the Fourier transformed signal. Further, a two-dimensional cross-sectional image of the target object 7 can be obtained as an intensity distribution of scattered or reflected light by the surface and inside of the target object 7 by performing a series of the above processing on spectrum interference data acquired by driving the galvanometer mirrors 3b, 3c.

The storage 6c contains cross-sectional images in time series, necessary data for estimating a later-described interference or border area and for calculating infiltration speed such as a scale of cross-sectional image, time at which a cross-sectional image is obtained, and a software program by which the signal processor 6c perform necessary processing. The display 6d displays at least cross-sectional images.

According to the present embodiment the target object 7 includes a transparent scattering suppressing material 12 on the front surface 7a. The transparent scattering suppression material 12 can be, for example, an adhesive sheet made from an adhesive material which poorly infiltrates into the target object, for example, one with a high transparency relative to the wide-band light beam P1. The adhesive sheet is used because tight adhesion to the front surface 7a is needed for the purpose of avoiding optical reflection or scattering by the front surface 7a. This can increase the amount of transmissive light and improve the S/N ratio of a cross-sectional image. The adhesive sheet is preferably one having adhesion and plasticity.

An excessively large optical feedback as scattered and reflected light by the front surface 7a of the target object 7 relatively decreases the amount of the spot light beam P5 infiltrated into the target object 7. This may hinder the generation of a cross-sectional image. However, with the transparent scattering suppression material 12, scattered light from the front surface 7a is reduced so that the amount of the spot light beam P5 infiltrated into the target object 7 can be relatively increased.

Moreover, it is easy to separate the scattered and reflected light from the surface 12a of the transparent scattering suppression material 12 and from the front surface 7a of the target object 7 since the surfaces 7a, 12a are away from each other. This makes it easier to acquire image intensity data on the basis of the optical feedback from the front surface 7a of the target object 7.

If it is difficult to attach the transparent scattering suppression material 12 on the front surface 7a, the front surface 7a can be smoothed to reduce the scattered light.

As described above, according to the present embodiment it is possible to prevent the scattered and reflected light from the inside of the target object 7 from being included in intense optical feedback from the front surface 7a. This accordingly leads to improving the measuring accuracy and generating clear cross-sectional images.

Figure 3A:
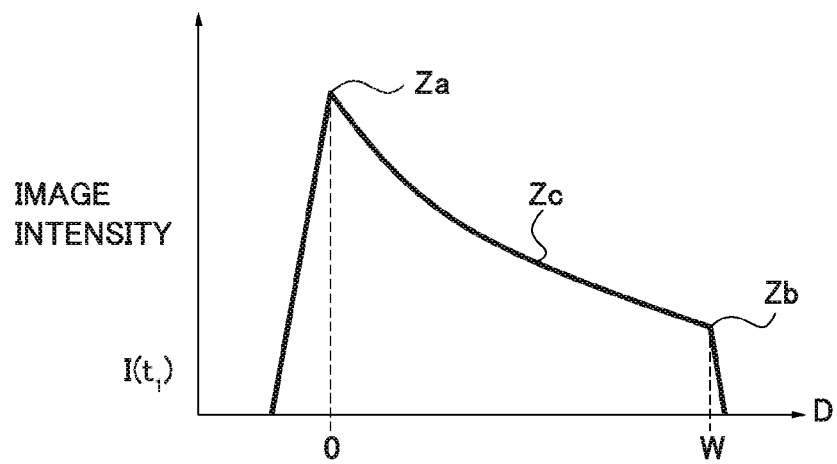
FIG. 3A is a graph showing a relation between the image intensity of a cross-sectional image and the depth of a target object in FIG. 2 at a certain time before the attachment of an infiltrative material to the target object.

Next, the measurement of the infiltration of the infiltrative material 9 into the target object 7 is described with reference to FIG. 3A to FIG. 3C, using a one-dimensional cross-sectional image, for example. For the sake of simplicity, the transparent scattering suppression material 12 is not used in FIGS. 3A to 3C. FIG. 3A shows a relation between the image intensity $I(t_1)$ of a cross-sectional image and the depth D of a target object along the optical axis or thickness (Z direction in FIG. 2) at time $t_1$ before the attachment of an infiltrative material to the target object. The depth D is measured from the front surface 7a. The location of the front surface 7a is set to depth 0 and the value of depth D is increased from the front surface 7a to the back surface 7b. The maximal value of the depth D signifies a thickness W of the target object 7.

At time $t_1$ the infiltrative material 9 is not attached to the target object 7. Therefore, the scattered and reflected light (optical feedback) from the front surface 7a is largest. In FIG. 3A the image intensity is a sharp rising line at the interface between the front surface 7a and air. The code Za indicates the image intensity $I(t_1)$ of the optical feedback by the interface between the front surface 7a and air at time $t_1$.

Microscopically, the target object 7 includes voids so that a part of the spot light beam P5 travels through the target object 7 and exits from the back surface 7b to outside. In FIG. 3A the image intensity is a sharp falling line due to an increase in transmissive light at the interface between the back surface 7b and air. The code Zb indicates the image intensity $I(t_1)$ of the optical feedback by the interface between the back surface 7b and air at time $t_1$.

Further, between the front surface 7a and back surface 7b inside the target object 7, in general the optical feedback exponentially decreases as the depth D increases. Thus, in FIG. 3A the image intensity is an exponential curve and the code Zc indicates the image intensity $I(t_1)$ of the optical feedback between the front surface 7a and back surface 7b at time $t_1$.

The fluid discharger as applicator 10 is driven to discharge fluids as the infiltrative material 9 to the back surface 7b of the target object 7. The fluids are permeated into the voids thereof over time from the back surface 7b to the front surface 7a, as shown in FIG. 2.

The time taken for the infiltrative material 9 to reach the front surface 7a largely differs depending on the relation between the target object 7 and infiltrative material 9, the thickness W of the target object 7, an ambient condition as temperature, and so on. It may be within one second or over several hours.

When the voids of the infiltrated area 11 are filled with the fluids of the infiltrative material 9, the physical optics of the interface 11a changes by reflection and refraction based on the Fresnel laws. That is, in general the amount of transmissive light increases more than that of scattered and reflected light on the interface 11a.

Figure 3B:
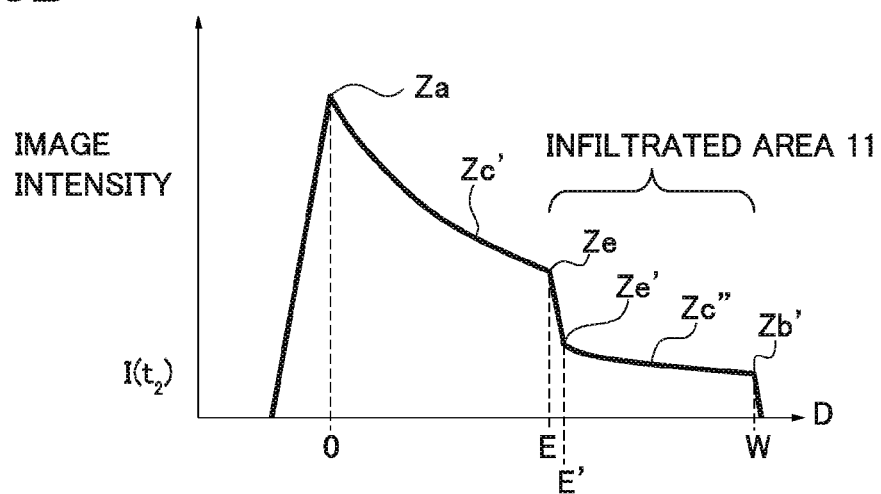
FIG. 3B is a graph showing a relation between the image intensity of a cross-sectional image and the depth of the target object in FIG. 2 at a certain time after the attachment of an infiltrative material to the target object.

FIG. 3B shows a relation between the image intensity $I(t_2)$ of a cross-sectional image and the depth D of the target object at time $t_2$ since time $\Delta t$ has elapsed from the attachment of the infiltrative material 9 to the target object 7. In the drawing the codes E and E' signify a depth from the front surface 7a to the interface 11a along the thickness. Herein, (E-E') is a line used for estimating the interface 11a, and a center value of this line is defined to be the interface, for example. Further, (D-E) or (D-E') signifies a depth of infiltration along the thickness of the back surface 7b to the interface 11a. The depth D is an optical path length and different from a depth equivalent to an actual distance. This is due to a distortion in the target object occurring depending on a magnitude and distribution of a refraction index n of the target object 7. The depth of the target object 7 equivalent to an actual distance in FIG. 3A can be found by dividing the thickness W as optical path length by a mean refraction index, for example.

At time $t_2$, the infiltrative material has not infiltrated between the front surface 7a and the depth E so that the image intensity $I(t_2)$ shows an exponential curve Zc' same as the exponential curve Zc at time $t_1$ and decreases. The code Ze indicates the image intensity $I(t_2)$ of the optical feedback at depth E of the interface 11a at time $t_2$.

At the interface 11a, the amount of transmissive light or refractive light of the spot light beam P5 is larger than that of scattered and reflected light due to a refractive phenomenon. Because of this, the light amount of optical feedback between the depths E and E' drastically decreases as that of the transmissive light increases, showing a sharp falling line in FIG. 3B. The code Ze' indicates the image intensity $I(t_2)$ of the optical feedback at depth E' at time $t_2$.

Reaching the infiltrated area 11, the transmissive light is partially reflected and scattered thereby to travel to the front surface 71 as optical feedback. A part of the rest thereof travels through the infiltrated area 11 and exits from the back surface 7b.

Generally, a difference in refractive index between air and the target object 7 is different from that between a fluid and the target object 7. Therefore, an exponential decrease in the amount of optical feedback reflected and scattered between the depth E' and the back surface 7b to travel to the front surface 7a differs from that in the amount of optical feedback reflected and scattered between the front surface 7a and depth E to travel to the front surface 7a. In FIG. 3B the code Zc" indicates an exponential curve of the image intensity $I(t_2)$ of the optical feedback between the depth E' and the back surface 7b at time $t_2$.

The amount of optical feedback relatively decreases at the interface between the back surface 7b and air as that of the transmissive light increases. The code ZB' in FIG. 3B indicates the image intensity $I(t_2)$ of the optical feedback at the interface between the back surface 7b and air.

Figure 3C:
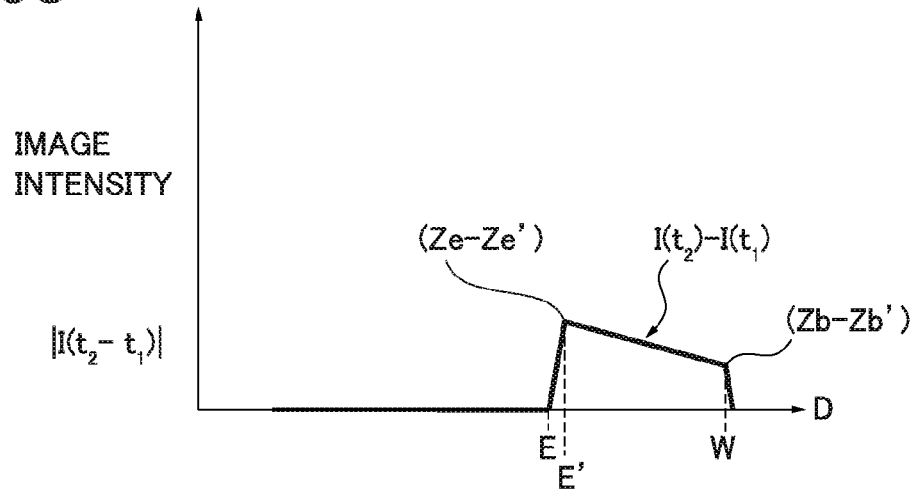
FIG. 3C is a graph showing a relation between the depth of the target object and a differential image intensity obtained from a difference in image intensity between the cross-sectional images in FIGS. 3A and 3B.

Accordingly, an absolute value $(I(t_2)-I(t_1))$ of a difference in image intensity in FIG. 3C can be obtained by finding an absolute value of a difference between the image intensity $I(t_2)$ at time $t_2$ and the image intensity $I(t_1)$ at time $t_1$.

The initial rising of the interface 11a of the infiltrated area 11 can be extracted according to the absolute value of the difference $(I(t_2)-I(t_1))$.

In other words, the infiltration position of the infiltrative material 9 at time $t_2$ can be estimated by estimating the depths E, E'. Also, the position of the interface 11a of the infiltrated area 11 is estimated by processing cross-sectional images obtained with different intervals of time $\Delta t = t_2 - t_1$. Infiltration speed along the thickness can be calculated by dividing a change in the estimated position of the interface 21a by the time $\Delta t$.

Next, the image processing of the signal processing controller 6 is described in detail. The controller 6a turns on the light source 1a by the control program and drives the galvanometer mirrors 3b, 3c, to two-dimensionally scan the front surface 7a of the target object 7. Thereby, image intensity data or brightness data is acquired momentarily to form a three-dimensional cross sectional shape of the target object 7 from the front surface 7a to the back surface 7b. The image intensity data is temporarily stored in the storage 6c together with information on scan position.

The signal processor 6b forms a three-dimensional cross-sectional image on the basis of the image intensity data. It also calculates a mean value of the image intensity data at the depth D. The mean value of the image intensity data corresponds to the image intensity $I(t_1)$ of the optical feedback at time $t_1$ in FIG. 3A.

Then, the controller 6a drives the fluid discharger as applicator 10 at time $t_1$ to attach fluids to the back surface 7b of the target object 7. The front surface 7a of the target object 7 is continuously scanned with the scan spot light beam P5 two-dimensionally to obtain image intensity data momentarily. The image intensity data is accumulated in the storage 6c.

Figure 4A:
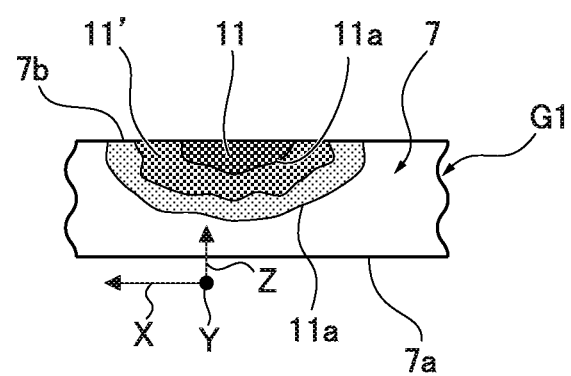
FIG. 4A shows an example of a two-dimensional cross-sectional image.
Figure 4B:
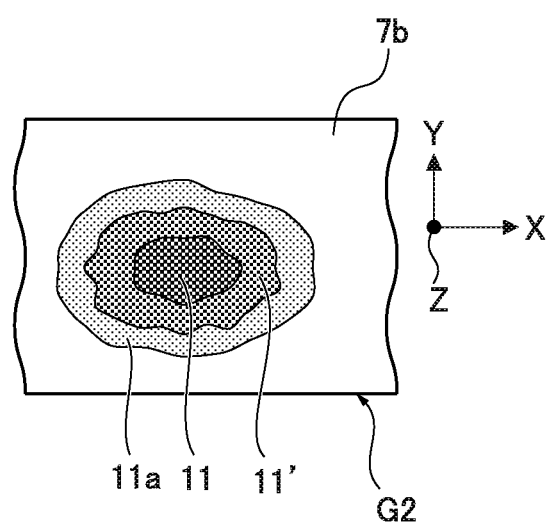
FIG. 4B shows an example of a two-dimensional planar image.

The signal processor 6b continuously forms a three-dimensional cross sectional image according to the image intensity data in the storage 6c. Instead of the three-dimensional cross-sectional image, a two-dimensional cross-sectional image G1 including the optical axis Z of the target object 7 and scan direction X orthogonal to the optical axis Z in FIG. 4A or including the optical axis Z and scan direction Y orthogonal to both of the optical axis Z and scan direction X can be created. Also, a two-dimensional planar image G2 in FIG. 4B in a two-dimensional plane parallel to a plane including the scan directions X and Y can be created.

For forming the two-dimensional cross-sectional image G1, either of the galvanometer mirrors 3b, 3c has to be reciprocatively driven. The controller 6a stores three-dimensional cross-sectional images, two-dimensional cross-sectional images G1, or two-dimensional planar images in time series in the storage 6c.

According to an instruction from the controller 6a, the display 6d displays the three-dimensional cross-sectional image, two-dimensional cross-sectional image G1, or two-dimensional planar image from the storage 6c when necessary. The two-dimensional cross-sectional image G1 on display changes over time along with the infiltration of the infiltrative material 9.

The signal processor 6b calculates mean image data along the thickness of the target object 7 from several dozen two-dimensional cross-sectional images G1 captured around time $t_1$, for example. Thus, mean image data with an image intensity corresponding to the image intensity $I(t_1)$ of the cross-sectional image at time $t_1$ in FIG. 3A can be found.

Alternatively, such mean image data can be obtained by temporally integrating brightness of each pixel and dividing it by time t or by making groups of several pixels, integrating brightness data on each pixel of each group, and dividing it by the number of pixels to obtain a mean value.

Likewise, the signal processor 6b calculates, for example, mean image data along the thickness of the target object 7 from several dozen two-dimensional cross-sectional images G1 captured around time $t_2$. Thus, mean image data with an image intensity corresponding to the image intensity $I(t_2)$ of the cross-sectional image in FIG. 3B can be obtained.

Further, the signal processor 6b creates mean differential image data by subtracting the mean image data with the image intensity $I(t_1)$ at time $t_1$ from that with the image intensity $I(t_2)$ at time $t_2$.

The signal processor 6b forms a differential image on the basis of the mean differential image data and displays it on the display 6d when necessary upon receipt of an instruction from the controller 6a. An observer can know an infiltrated state of the infiltrative material 9 in the target object 7 from the differential image on the display 6d.

Moreover, the signal processor 6b can estimate a mean value of the depth of infiltration (D-E) or (D-E') at time $t_2$ by finding the mean value of the depths E, E' from the mean differential image data. That is, the initial rising representing the position of the interface 11a is extracted from the mean differential image data.

Further, the signal processor 6b finds a mean infiltration speed of the infiltrative material 9 relative to the target object 7 by dividing the mean value of the infiltration depth (D-E') or (D-E) by time Δt. The estimated mean value of the infiltration depth (D-E) or (D-E') and mean infiltration speed are displayed on the display 6d when needed.

Thus, the signal processor 6b obtains a differential image from the two-dimensional cross-sectional image G1 of the target object in the depth direction and the direction orthogonal to the depth direction stored in the storage. Then, the position of the interface 11a or the initial rising of the image intensity is extracted by image processing.

Accordingly, the signal processor 6b functions as an estimator to estimate the position of the interface 11a of the infiltrated area 11 and calculates the infiltration speed by dividing, by time Δt, an estimated position of the interface 11a along the thickness from the cross-sectional images obtained at different times. Further, an estimated position of the interface 11a of the infiltrated area 11 and infiltration speed along the plane can be calculated from a temporal change in the two-dimensional planar image G2.

In the present embodiment the mean differential image data is obtained at times $t_1$ and $t_2$. Alternatively, the filtration of the infiltrative material 9 into the target object 7 can be dynamically displayed on the display 6d over time by calculating the mean differential image data momentarily.

Depending on a combination of the target object 7 and the infiltrative material 9, the amount of reflected light of the spot light beam P5 may be larger than that of transmissive light due to the reflection by the interface 11a of the infiltrated area 11. However, even in this case, image intensity still changes at the interface 11a so that the position of the interface 11a can be estimated to calculate the infiltration speed.

As described above, according to the present embodiment the measuring light beam P2 is projected to the front surface 7a of the target object 7 while the infiltrative material 9 is attached onto the back surface 7b of the target object 7, to thereby measure the infiltration state of the infiltrative material 9. In addition, a change in the intensity of the scattered and reflected light from the interface of the infiltrated area 11 is emphasized by using an optical interference phenomenon. Therefore, it is possible to continuously observe the infiltration state of the infiltrative material 9 in a deep portion of the target object 7 without destroying or damaging the target object 7 and without receiving an influence from the reflection by the infiltrative material 9.

Although the present invention has been described in terms of exemplary embodiments, it is not limited thereto. It should be appreciated that variations or modifications may be made in the embodiments described by persons skilled in the art without departing from the scope of the present invention as defined by the following claims.

What is claimed is:

1. An infiltration measuring device which measures an infiltration of an infiltrative material into a target object, comprising:
 a light source;
 an optical splitter configured to split a light beam from the light source into a reference light beam and a measuring light beam;
 a reference optical system provided in an optical path of the reference light beam;
 a measuring optical system provided in an optical path of the measuring light beam and configured to measure the target object;
 an optical combiner configured to combine an optical feedback from the target object with a light beam from the reference optical system;
 a detector configured to detect the light beam combined by the optical combiner and convert the combined light beam into a photoelectric conversion signal;
 an imager configured to image a cross section of the target object on the basis of the photoelectric conversion signal;
 a display configured to display a cross-sectional image formed by the imager;
 an applicator configured to apply the infiltrative material onto the target object;
 a storage configured to store the cross-sectional image of the target object in time series; and
 an estimator configured to,
  estimate a position of an interface of an infiltrated area of the infiltrative material applied on the target object on the basis of a temporal change in the cross-sectional image stored in the storage by,
   obtaining a differential image from a two-dimensional cross-sectional image of the target object in a depth direction and a direction orthogonal to the depth direction, and
   estimating the position of the interface of the infiltrated area by extracting an initial rising of an image intensity of the differential image in the depth direction.

2. The infiltration measuring device according to claim 1, wherein
 the infiltrative material is a fluid.

3. The infiltration measuring device according to claim 2, wherein
 the applicator is a fluid discharger to quantitatively discharge a fluid.

4. The infiltration measuring device according to claim 1, wherein
 the applicator is provided on a side of a surface of the target object opposite to a surface on which the measuring light beam is incident.

5. The infiltration measuring device according to claim 1, wherein
 the estimator is configured to estimate the position of the interface of the infiltrated area from cross-sectional images obtained at different times and calculate an infiltration speed of the infiltrative material into the target object in the depth direction by dividing an estimated position of the interface by the times.

6. The infiltration measuring device according to claim 1, wherein
 the target object is a sheet-like medium or a printed material.

7. The infiltration measuring device according to claim 1, wherein
 the target object includes a transparent scattering suppression material on a front surface.

8. The infiltration measuring device according to claim 1, wherein
the light source is configured to project a light beam in a wide band having a center wavelength in a near-infrared wavelength band.

9. An infiltration measuring method comprising:
attaching an infiltrative material to a back surface of a target object while projecting a light beam onto a front surface of the target object;
imaging a temporal change in a cross section of the target object using the projected light beam to obtain a cross-sectional image;
storing, in a storage, the cross-sectional image of the target object in time series; and
observing an infiltration of the infiltrative material into the target object by,
  estimating a position of an interface of an infiltrated area of the infiltrative material applied on the target object on the basis of a temporal change in the cross-sectional image stored in the storage, the estimating including,
    obtaining a differential image from a two-dimensional cross-sectional image of the target object in a depth direction and a direction orthogonal to the depth direction, and
    estimating the position of the interface of the infiltrated area by extracting an initial rising of an image intensity of the differential image in the depth direction.

* * * * *